United States Patent [19]

Grosselin et al.

[11] Patent Number: 4,929,776

[45] Date of Patent: * May 29, 1990

[54] PROCESS FOR THE PREPARATION OF UNSATURATED ALCOHOLS

[75] Inventors: Jean-Michel Grosselin; Claude Mercier, both of Lyon, France

[73] Assignee: Rhone-Poulenc Sante, Antony, France

[*] Notice: The portion of the term of this patent subsequent to May 15, 2007 has been disclaimed.

[21] Appl. No.: 277,306

[22] Filed: Nov. 29, 1988

[30] Foreign Application Priority Data

Dec. 1, 1987 [FR] France ................... 87 16628

[51] Int. Cl.$^5$ ................. C07C 29/14; C07C 27/04
[52] U.S. Cl. ..................... 568/862; 568/813; 568/843; 568/846; 568/861
[58] Field of Search ............... 568/862, 880, 813, 843, 568/846, 861

[56] References Cited

U.S. PATENT DOCUMENTS

| | | | |
|---|---|---|---|
| 3,935,284 | 1/1976 | Kruse | 568/862 |
| 4,024,193 | 5/1977 | Kruse | 568/862 |
| 4,268,454 | 5/1981 | Pez et al. | 568/880 |
| 4,317,946 | 3/1982 | Costa | 568/862 |
| 4,321,414 | 3/1982 | Costa | 568/862 |
| 4,418,227 | 11/1983 | Pez et al. | 568/880 |
| 4,429,056 | 1/1984 | Smith | 568/880 |
| 4,514,521 | 4/1985 | Smith | 568/880 |
| 4,777,302 | 10/1988 | Haji et al. | 568/862 |

FOREIGN PATENT DOCUMENTS

| | | | |
|---|---|---|---|
| 0295890 | 12/1988 | European Pat. Off. | 568/862 |
| 0297752 | 1/1989 | European Pat. Off. | 568/862 |
| 0140030 | 8/1983 | Japan | 568/862 |
| 2024816 | 1/1980 | United Kingdom | 568/862 |

*Primary Examiner*—Werren B. Lone
*Attorney, Agent, or Firm*—Stevens, Davis, Miller & Mosher

[57] ABSTRACT

Unsaturated alcohols are prepared by hydrogenation of the corresponding unsaturated carbonyl compounds in a homogeneous medium and in the presence of a ruthenium-based catalyst.

10 Claims, No Drawings

PROCESS FOR THE PREPARATION OF UNSATURATED ALCOHOLS

The present invention relates to the preparation of primary or secondary unsaturated alcohols by hydrogenation of the corresponding aldehydes or ketones.

More particularly, the present invention provides a process for the preparation of unsaturated alcohols of the formula:

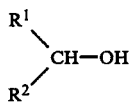

in which each of $R^1$ and $R^2$, which are identical or different, represents a hydrogen atom, a saturated or unsaturated aliphatic radical optionally substituted by a saturated or unsaturated alicyclic radical or by an aromatic radical, a saturated or unsaturated alicyclic radical or an aromatic radical, at least one of $R^1$ and $R^2$ containing an ethylenic double bond, or $R^1$ and $R^2$ together form an unsaturated alicyclic radical, each of the aforesaid aliphatic, alicyclic or aromatic radicals being optionally substituted by one or more identical or different alkyl radicals of 1 to 4 carbon atoms, hydroxyl radicals, or alkoxy radicals of 1 to 4 carbon atoms, which comprises hydrogenating a carbonyl compound of the formula:

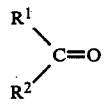

in which $R^1$ and $R^2$ are as defined above, in a homogeneous liquid medium, with hydrogen in the presence of a ruthenium-based catalyst.

More particularly, the present invention provides a process for the preparation of α,β-unsaturated alcohols from the corresponding α,β-unsaturated carbonyl compounds, i.e. for the preparation of the products of formula (I) in which at least one of the radicals $R^1$ and $R^2$ contains a double bond in the α,β-position relative to the alcohol group, from the corresponding α,β-unsaturated compounds of formula (II).

The invention is especially useful for the preparation of α,β-unsaturated alcohols of formula (I) in which one of the symbols $R^1$ and $R^2$ represents a hydrogen atom and the other represents an aliphatic radical containing 1 to 30 carbon atoms and at least one double bond in the α,β-position relative to the alcohol group, which is optionally substituted by one or more identical or different radicals selected from alkyl radicals containing 1 to 4 carbon atoms, hydroxyl radicals and alkoxy radicals of which the alkyl part contains 1 to 4 carbon atoms, by an alicyclic radical containing 5 or 6 carbon atoms, which is saturated or unsaturated and optionally substituted by one or more alkyl radicals containing 1 to 4 carbon atoms, or by an optionally substituted phenyl radical, or alternatively $R^1$ and $R^2$ together form an unsaturated alicyclic radical optionally substituted by one or more alkyl radicals containing 1 to 4 carbon atoms, from the corresponding α,β-unsaturated carbonyl compounds of formula (II).

More particularly, the present invention provides a process for the preparation of prenol from prenal, nerol/geraniol from citral, crotyl alcohol from crotonaldehyde or cinnamyl alcohol from cinnamaldehyde.

Carbon-carbon double bonds are easy to hydrogenate using homogeneous catalysis, but carbonyl groups are different to reduce by this means, especially when they are present in an unsaturated compound and retention of the unsaturated is desired.

It is known to use organometallic complexes based on rhodium [T. Mizoroki et al., Bull. Chem. Soc. Japan, 50, 2148 (1977)] or based on iridium [E. Farnetti et al., J. Chem. Soc. Chem. Comm., p. 746 (1986)] for the selective reduction of cinnamaldehyde to the corresponding unsaturated alcohol. W. Strohmeier and K. Kolke, J. Organometal. Chem. 193, c63 (1980), have described the reduction of crotonaldehyde by means of ruthenium complexes, the best selectivity being obtained with $RuCl_2[P(C_6H_{11})_3]_2(CO)_2$. Finally, K. Hotta, J. Mol. Catal., 29, 105-107 (1985), has shown that citral is converted to geraniol/nerol by hydrogenation in the presence of a complex $RuCl_2[(PPh_3)]_3$, the reaction being carried out in a toluene/ethanol mixture and in the presence of excess hydrochloric acid.

By using the process of the present invention, unsaturated carbonyl compounds of formula (II) are selectively converted into saturated alcohols of formula (I). The hydrogenation catalyst used is preferably a hydride or halogen derivative of ruthenium complexed by a ligand or associated with a ligand, which may be generated in situ.

Particularly suitable ruthenium derivatives are $RuH_2(PPh_3)_4$, which can be prepared by the method of R. O. Harris et al., J. Organometal. Chem. 54, 259-264 (1973), $RuH(OAc)(PPh_3)_4$, which can be prepared according to Inorg. Synthesis, 16, p. 53 and 75 to 79, and $RuCl_2(PPh_3)_4$.

Interesting results are also obtained by using ruthenium derivatives selected from inorganic salts and oxides of ruthenium, in the presence of a ligand which is preferably a phosphine such as triphenylphosphine ($PPh_3$) or tri(metasulphophenyl)phosphine(TPPTS). It can be advantageous to use a catalyst system resulting from the association of a ruthenium chloride ($RuCl_3 \cdot xH_2O$) with triphenylphosphine or tri(metasulphophenyl)phosphine.

The hydrogenation is generally carried out at a temperature of between 0° and 100° C., preferably of between 20° and 50° C., in an organic solvent. It is particularly advantageous to carry out the reaction under a pressure of between 1 and 200 bar, preferably of between 1 and 20 bar.

The organic solvent used is preferably a polar solvent which is an alcohol (methanol, ethanol, isopropanol), optionally associated with a non-polar solvent selected from aliphatic hydrocarbons (pentane, hexane, heptane, octane), alicyclic hydrocarbons (cyclohexane), and aromatic hydrocarbons (benzene, toluene, xylene), an ether (diethyl ether, diisopropyl ether), or an ester (methyl acetate, ethyl acetate, butyl acetate).

It is particularly advantageous to add to the polar solvent, or the solvent mixture, up to 35% of the total volume of water, in order to keep the medium homogeneous.

In general, from 0.1 to 0.001 mol of catalyst is used per mol of α,β-unsaturated aldehyde of formula (II).

The process of the present invention makes it possible to obtain the unsaturated alcohols of formula (I) with a selectivity which is generally greater than 80%.

The following Examples illustrate the invention.

EXAMPLE 1

RuH$_2$(PPh$_3$)$_4$ (0.05 g; 0.43 mmol), prenal (8.7 g; 0.103 mol), isopropanol (82 g) and water (4 g) are introduced successively into a 300 cc reactor of the SOTELEM type which has been purged with nitrogen beforehand. After purging 3 times with nitrogen and then 3 times with hydrogen under a pressure of 20 bar, the hydrogen pressure is set at 30 bar and the reaction mixture is then heated to 50° C. The stirring is adjusted to 1200 rpm.

After 2 hours 40 minutes, analysis by gas chromatography (Rheoplex 400 column; Chromosorb PAM; length 2.5 m; diameter 3 mm; isothermal analysis at 130° C.) shows that:
the degree of conversion of the prenal is 100%, and
the distribution of the hydrogenation products is as follows:

| | |
|---|---|
| prenol | 90.6% |
| isoamyl alcohol | 4% |
| isovaleraldehyde | not detectable |

EXAMPLE 2

The procedure is the same as in Example 1 except that RuCl$_2$(PPh$_3$)$_4$ (0.43 mmol) is used.

After 180 minutes, analysis by gas chromatography shows that:
the degree of conversion of the prenal is 80%, and
the distribution of the hydrogenation products is as follows:

| | |
|---|---|
| prenol | 65% |
| isoamyl alcohol | 7% |
| isovaleraldehyde | 4% |

The selectivity in respect of prenol is 81%.

EXAMPLE 3

The procedure is the same as in Example 1 except that RuH(OAc)(PPh$_3$)$_3$ (0.36 mmol) is used.

After 7 hours 10 minutes, analysis by gas chromatography shows that:
the degree of conversion of the prenal is 80%, and
the distribution of the hydrogenation products is as follows:

| | |
|---|---|
| prenol | 44% |
| isoamyl alcohol | 5% |
| isovaleraldehyde | 4% |

The selectivity in respect of prenol is 73%.

EXAMPLE 4

The following are introduced successively into a 25 cc glass flask:

| | |
|---|---|
| RuCl$_3$.3H$_2$O | 9.5 × 10$^{-5}$ mol |
| triphenylphosphine | 4.24 × 10$^{-4}$ mol |
| isopropanol | 8.5 g |
| water | 1 g |
| prenal | 19 × 10$^{-3}$ mol |

The flask is introduced into a 125 cc autoclave placed in an enclosure which permits shaking. After purging 3 times with hydrogen, the temperature is set at 35° C. and the pressure at 23 bar.

After 2 hours 40 minutes, analysis by gas chromatography shows that:
the degree of conversion of the prenal is 72%, and
the distribution of the hydrogenation products is as follows:

| | |
|---|---|
| prenol | 70% |
| isoamyl alcohol | 1.2% |
| isovaleraldehyde | 0.6% |

The selectivity in respect of prenol is 97%.

EXAMPLE 5

The following are introduced successively into a 25 cc flask:

| | |
|---|---|
| RuCl$_3$.3H$_2$O | 10$^{-4}$ mol |
| TPPTS | 4.3 × 10$^{-4}$ mol |
| isopropanol | 9 g |
| water | 4 g |
| prenal | 20 × 10$^{-3}$ mol |

The flask is introduced into a 125 cc autoclave placed in an enclosure which permits shaking. After purging with hydrogen, the temperature is set at 36° C. and the pressure at 20 bar.

After 3 hours 30 minutes, analysis by gas chromatography shows that:
the degree of conversion of the prenal is 89%, and
the distribution of the hydrogenation product is as follows:

| | |
|---|---|
| prenol | 88% |
| isoamyl alcohol | 1% |

The selectivity in respect of prenol is 98%.

EXAMPLE 6

The following are introduced successively into a 25 cc glass flask:

| | |
|---|---|
| RuCl$_3$.3H$_2$O | 1.22 × 10$^{-4}$ mol |
| triphenylphosphine | 4.7 × 10$^{-4}$ mol |
| toluene | 7 cc |
| ethanol | 3 cc |
| citral | 9.4 × 10$^{-3}$ mol |

The flask is introduced into a 125 cc autoclave placed in an enclosure which permits shaking. After purging 3 times with hydrogen, the temperature is set at 35° C. and the hydrogen pressure at 50 bar.

After 7 hours, analysis by gas chromatography shows that:
the degree of conversion of the citral is 96%, and
the distribution of the hydrogenation products is as follows:

| | |
|---|---|
| nerol/geraniol | 96% |
| citronellol | 1.3% |
| citronellal | not detectable |
| tetrahydrogeraniol | 0.4% |

The selectivity in respect of nerol/gernoil is 97%.

We claim:

1. A process for the preparation of an unsaturated alcohol of the formula:

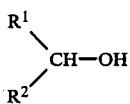

in which each of $R^1$ and $R^2$, which are identical or different, represents a hydrogen atom, a saturated or unsaturated aliphatic radical of 1 to 30 carbon atoms, a saturated or unsaturated aliphatic radical of 1 to 30 carbon atoms substituted by a saturated or unsaturated alicyclic radical of 5 or 6 carbon atoms by a phenyl radical, a saturated or unsaturated alicyclic radical of 5 or 6 carbon atoms or a phenyl radical, at least one of the radicals $R^1$ and $R^2$ containing an ethylenic double bond, or $R^1$ and $R^2$ together form an ethylenically unsaturated alicyclic radical of 5 or 6 carbon atoms, each of the aforesaid aliphatic, alicyclic or phenyl radicals being unsubstituted or substituted by one or more identical or different alkyl radicals of 1 to 4 carbon atoms, which comprises hydrogenating a carbonyl compound of the formula:

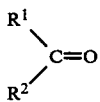

in which $R^1$ and $R^2$ are as defined above, in a homogeneous liquid medium with hydrogen in the presence of a neutral ruthenium-based catalyst."

2. Process according to claim 1, wherein the catalyst is a hydride or halogen derivative of ruthenium complexed by a ligand or associated with a ligand, which may be generated in situ.

3. Process according to claim 2, wherein the catalyst is $RuH_2(PPh_3)_4$, $RuH(OAc)(PPh_3)_4$, $RuCl_2(PPh_3)_4$, or an association of a salt or oxide of ruthenium with a phosphine ligand.

4. Process according to claim 3, wherein the catalyst consists of an association of a ruthenium halide with a phosphine ligand.

5. Process according to claim 4 wherein the ruthenium halide is ruthenium chloride, $RuCl_3.3\ H_2O$, and the phosphine is triphenylphosphine or tri(metasulphophenyl)phosphine.

6. Process according to claim 1 wherein the reaction is carried out in a polar organic solvent which is an alcohol, optionally associated with an aliphatic, cycloaliphatic or aromatic hydrocarbon, an ether or an ester.

7. Process according to claim 6, wherein the solvent or solvent mixture contains up to 35% of its total volume of water.

8. Process according to claim 1, wherein the reaction is carried out under a pressure of between 1 and 200 bar.

9. Process according to claim 1 wherein the reaction is carried out at a temperature of between 0° and 100° C.

10. Process according to claim 1, wherein prenal is hydrogenated selectively to prenol or citral to geraniol/nerol.

* * * * *